US006265638B1

(12) United States Patent
Bidney et al.

(10) Patent No.: US 6,265,638 B1
(45) Date of Patent: Jul. 24, 2001

(54) METHOD OF PLANT TRANSFORMATION

(75) Inventors: Dennis L. Bidney, Urbandale; Christopher Jay Scelonge, Des Moines, both of IA (US)

(73) Assignee: Pioneer Hi-Bred International, Inc., Des Moines, IA (US)

( * ) Notice: Subject to any disclaimer, the term of this patent is extended or adjusted under 35 U.S.C. 154(b) by 0 days.

(21) Appl. No.: 09/407,574

(22) Filed: Sep. 28, 1999

Related U.S. Application Data (60) Provisional application No. 60/102,638, filed on Oct. 1, 1998.

(51) Int. Cl.[7] ............................ C12N 15/82; C12N 15/84; A01H 1/00
(52) U.S. Cl. .................. 800/294; 435/320.1; 435/252.3; 435/252.2; 435/410; 435/468; 435/469; 435/430; 800/278
(58) Field of Search ............................... 435/320.1, 430, 435/252.2, 252.3, 468, 469, 6, 91.4, 410; 800/278, 294

(56) References Cited

U.S. PATENT DOCUMENTS 5,538,878 * 7/1996 Thomas et al. .................... 435/172.3

OTHER PUBLICATIONS

Bevan, Michael, Binary Agrobacterium Vectors for Plant Transformation, Nucleic Acids Research, 1984, pp. 8711–8721, vol. 12, No. 22, IRL Press Limited, Oxford, England.

Watson et al., New Cloning Vehicles for Transformation of Higher Plants, EMBO Journal, 1985, pp. 277–284, vol. 4, No. 2, IRL Press Limited, Oxford, England.

Depicker et al., Frequencies of Simulataneous Transformation With Different T–DNAs and Their Relevance to the Agrobacterium/Plant Cell Interaction, Biol. Gen. Genet, pp. 477–484, vol. 201, MGG, Springer–Verlag.

Simpson et al., A Disarmed Binary Vector from *Agrobacterium Tumefaciens* Functions in *Agrobacterium Tumefaciens* Functions in Agrobacterium Rhizogenes, Plant Molecular Biology, 1986, pp. 403–415, vol. 6, Martinus Nijhoff Publishers, Dordrecht—Printed in the Netherlands.

de Framond et al., Two Unlinked T–DNAs Can Transform The Same Tobacco Plant Cell and Segregate in the F1 Generation, Biol. Gen. Ganet, 1986, pp. 125–131, vol. 202, MGG Springer–Verlag.

McKnight et al., Segregation of Genes Transferred to One Plant Cell From Two Separate Agrobacterium Strains, Patent Molecular Biology, 1987, pp. 439–445, vol. 8, Martinus Nijhoff Publishers, Dordrecht—Printed in the Netherlands.

Hooykmass, Paul, J.J., Agrobacterium Molecular Genetics, Pllant Molecular Biology Manual, 1988, pp.1–13, vol. A4, Kluwer Academic Publishers, Dordrechtp—Printed in Belgium.

An et al., Binary Vectors, Plant Molecular Biology Manual, 1988, pp. 1–19, vol. A3, Kluwer Academic Publishers, Dordrecht—Printed in Belgium.

De Block et al., Two T–DNA's Co–Transformed into *Brassica Napus* by a Double *Agrobacterium Tumefaciens* Infection are Mainly Integrated at the Same Locus, Theor. Appl. Genet, 1991, pp. 257–263, vol. 82, Plant Genetic Systems, N.V., Jozef Plateaustraat 22, 900 Gent, Belgium.

Walkerpeach et al., Agrobacterium–Mediated Gene Transfer to Plant Cells: Cointegrate and Binary Vector Systems, Plant Molecular Biology Manual, 1994, pp. 1–19, vol. B1, 1994 Kluwer Academic Publishers, Belgium.

Frishch et al., Complete Sequence of the Biary Vector Bin 19, Plant Molecular Biology, 1995, pp. 405–409, vol. 27, 1995 Kluwer Academic Publishers, Belgium.

Komari et al., Vectors Carrying Two Separate T–DNAs for Co–Transformation of Higher Plants Mediated by *Agrobacterium Tumefaciens* and Segregation of Transformants Free from Selection Markers, The Plant Journal, 1996, pp. 165–174, vol. 10(1).

van Engelen et al., pBINPLUS: An Improved Plant Transformation Vector Based on:pBIN19, Transgenic Research, 1995, pp. 288–290, vol. 4, Chapman & Hall.

A Binary–BAC System for Plant Transformation With High–Molecular–Weight DNA, C. Hamilton, Gene 200, 1997, pp. 107–116.

High Efficiency Transformation of Maize (*Zea mays* L.) Mediated by *Agrobacterium Tumefaciens*, Y. Ishida et al., Nature Biotechnology, vol. 14, Jun. 1996, pp. 745–750.

* cited by examiner

Primary Examiner—David Guzo
(74) Attorney, Agent, or Firm—Alston & Bird LLP (57) ABSTRACT

Compositions and methods for the efficient co-transformation of a plant are provided. Novel compositions are Agrobacterium strains that have been engineered to comprise at least two binary vector plasmids in addition to a helper plasmid comprising the vir functions. Each of the binary vectors comprises its own T-DNA borders flanking a heterologous nucleotide sequence of interest. Methods of the invention comprise the use of these novel multiple-binary vector Agrobacterium strains to co-transform a plant. In this manner, heterologous nucleotide sequences of interest residing on different binary vectors can be independently introduced into the plant in a single transformation event and incorporated in the plant's nuclear DNA in an unlinked manner. The invention also provides for regenerated, fertile transgenic plants, transgenic seeds produced therefrom, and T1 and subsequent generations.

23 Claims, 4 Drawing Sheets

METHOD OF PLANT TRANSFORMATION

CROSS-REFERENCE TO RELATED APPLICATION

This application claims the benefit of U.S. Provisional Application No. 60/102,638, filed Oct. 1, 1998.

FIELD OF THE INVENTION

The present invention relates to methods and compositions for the transformation of plants, more particularly to methods for transformation utilizing Agrobacterium.

BACKGROUND OF THE INVENTION

Agrobacterium, a natural plant pathogen, has been widely used for the transformation of dicotyledonous plants and more recently for transformation of monocotyledonous plants. The advantage of the Agrobacterium-mediated gene transfer system is that it offers the potential to regenerate transgenic cells at relatively high frequencies without a significant reduction in plant regeneration rates. Moreover, the process of DNA transfer to the plant genome is well characterized relative to other DNA delivery methods. DNA transferred via Agrobacterium is less likely to undergo any major rearrangements than is DNA transferred via direct delivery, and it integrates into the plant genome often in single or low copy numbers.

Currently the most commonly used Agrobacterium-mediated gene transfer system is a binary transformation vector system where the Agrobacterium has been engineered to include a disarmed, or nononcogenic, Ti helper plasmid, which encodes the vir functions necessary for DNA transfer, and a much smaller separate plasmid called the binary vector plasmid, which carries the transferred DNA, or the T-DNA region. The T-DNA is defined by sequences at each end, called T-DNA borders, which play an important role in the production of T-DNA and in the transfer process.

Agrobacterium-mediated introduction of multiple genes, or so-called co-transformation, occurs naturally. In nature, the Ti plasmid of both the octopine producing strain, A348, and the A. rhizogenes strains have multiple T-DNA regions that transfer independently and integrate into the plant genome.

Co-transformation has been carried out with genetically engineered Agrobacterium strains. Introduction of multiple genes into plants using Agrobacterium-mediated transformation systems may result in linked or unlinked integration of T-DNA regions depending upon the method of co-transformation used. In some instances, a transformed plant may have both linked and unlinked integration of the T-DNA regions when multiple T-DNA regions are transferred. As a result, subsequent generations of transformed plants may retain only subsets of the originally transferred and integrated T-DNA regions. Such segregation of T-DNA regions carrying different genes may be desirable when the T-DNA region or regions that are lost to segregating progeny carry selectable marker genes that are desirable for selecting initial transformed plants, but are undesirable in the progeny of those transformed plants.

Co-transformation in engineered Agrobacterium binary vector systems has thus far been accomplished in three different ways. The first of these methods involves coinfection of a plant with two Agrobacterium strains, each of which has a unique T-DNA carried on identical binary vector plasmids (McNight et al. (1987) *Plant Mol. Biol.* 8:439–445) or different binary vector plasmids (DeNeve et al. (1997) *Plant J.* 11(1):15–29. Alternatively, co-transformation may be achieved by infection of a plant with a single Agrobacterium strain that has one T-DNA residing on the Ti helper plasmid and a second T-DNA residing on a binary plasmid (de Framond et al. (1986) *Mol. Gen. Genet.* 202:125–131). A third method of co-transformation involves infection of a plant with a single Agrobacterium strain having two separate T-DNA regions on a single binary plasmid (Komari et al. (1996) *Plant J.* 10(1):165–174). The first two methods favor unlinked integration of T-DNA regions, while the latter method favors linked integration of the T-DNA regions, though both types of integration may occur within one plant.

Given the advantages of Agrobacterium-mediated transformation systems and the need for simultaneous transformation of plants with more than one gene of interest, additional methods for efficient co-transformation using Agrobacterium are needed.

SUMMARY OF THE INVENTION

The present invention is drawn to novel compositions and methods for the efficient co-transformation of a plant. Novel compositions are Agrobacterium strains that have been engineered to comprise at least two binary vector plasmids in addition to a helper plasmid comprising the vir functions. Each of the binary vectors comprises its own T-DNA borders flanking a heterologous nucleotide sequence of interest. The heterologous nucleotide sequence within at least one of the T-DNA border sequences comprises at least one expression cassette expressing a coding sequence for a plant scorable marker gene. The nucleotide sequence of interest may additionally comprise at least one coding sequence of interest operably linked to regulatory regions that are functional within a host plant. Methods of the invention comprise the use of these novel compositions to co-transform a plant. In this manner, heterologous nucleotide sequences of interest residing on different binary vectors can be independently introduced into the plant in a single transformation event and incorporated in the plant's genome in an unlinked manner. The transferred nucleotide sequences will be flanked by their respective T-DNA borders and present in the transformed plant in low copy number.

Transformed plant cells, tissues, plants, and seed are also provided. Such transformed compositions are characterized by the presence of independently integrated T-DNA borders and a low copy number of the transferred nucleotide sequences. The invention encompasses regenerated, fertile transgenic plants, transgenic seeds produced therefrom, and T1 and subsequent generations.

DETAILED DESCRIPTION OF THE INVENTION

Compositions and methods for the efficient co-transformation of a plant are provided. Novel compositions are Agrobacterium strains that have been engineered to allow for co-transfer of at least two heterologous nucleotide sequences of interest in an independent manner. Methods of the invention comprise the use of these novel compositions for co-transformation of a plant.

By "co-transformation" is intended at least two independent transformation events wherein each independent event comprises the transfer of a heterologous nucleotide sequence into a plant cell and the subsequent stable integration of the transferred sequence into the plant genome. By "heterologous" is intended foreign, or not naturally occurring within the plant's genome prior to transformation. In accordance with the method of the present invention, co-transformation is achieved in a single transformation event with the use of Agrobacterium-mediated gene transfer.

Agrobacterium-mediated gene transfer exploits the natural ability of *Agrobacterium tumefaciens* and *A. rhizogenes* to transfer DNA into plant chromosomes. Agrobacterium is a plant pathogen that transfers a set of genes encoded in a region called T-DNA of its tumor-inducing (Ti) plasmid or hairy-root-inducing (Ri) plasmid into plant cells at wound sites. This process depends on the cis acting T-DNA border sequences that flank the transferred DNA and the trans acting virulence (vir) functions encoded by the Ti plasmid or Ri plasmid and the bacteria's chromosome. The typical result of gene transfer in *A. tumefaciens* is a tumorous growth called a crown gall. The result of gene transfer in *A. rhizogenes* is hairy root disease. In both cases, gene transfer results in stable integration of the T-DNA region into a plant host chromosome. The ability to cause crown gall disease or hairy root disease can be removed by deletion of the oncogenic genes in the T-DNA without loss of DNA transfer and integration. When the oncogenic genes are removed in this manner, the Agrobacterium is said to be disarmed or nononcogenic.

Such Agrobacterium-mediated gene transfer systems are modified to contain a heterologous or foreign nucleotide sequence of interest, such as a foreign gene or genes of interest, to be expressed in the transformed plant cells. The heterologous nucleotide sequence to be transferred is incorporated into the T-DNA region, which is flanked by imperfect 25-bp terminal repeats or T-DNA border sequences that define the end points of an integrated T-DNA. Any sequences between these terminal repeats become integrated into the plant nuclear DNA.

Gene transfer by means of engineered Agrobacterium strains has become routine for most dicotyledonous plants and for some monocotyledonous plants. See, for example, Fraley et al. (1983) *Proc. Natl. Acad. Sci. USA* 80:4803; Watson et al. (1985) *EMBO J.* 4:277; Horsch et al. (1985) *Science* 227:1229; Hernalsteens et al. (1984) *EMBO J.* 3:3039; Comai et al. (1984) *Nature* 317:741; Petit et al. (1986) *Mol. Gen. Genet.* 202:388-393; Shah et al. (1986) *Science* 233:478; Bytebier et al. (1987) Proc. Natl. Acad. Sci. USA 84:5345; Schafew et al. (1987) *Nature* 327:529; McKnight et al. (1987) *Plant Mol. Biol.* 8:439–445; Potrykus (1990) *Biotechnol* 8:535; Grimsley et al. (1987) *Nature* 325:177; Gould et al. (1991) *Plant Physiol.* 95:426; Ishida et al. (1996) *Nature Biotechnology* 14:745; and U.S. Pat. No. 5,591,616, and the references cited therein.

The ability of Agrobacterium to carry out this DNA transfer process is fully enabled when the T-DNA border sequences flanking the heterologous nucleotide sequence to be transferred and the vir functions are located on separate compatible plasmids. This fact has allowed for the development of binary vector systems where Agrobacterium strains are engineered to contain a Ti (or Ri in the case of *A. rhizogenes*) plasmid that comprises the vir functions, and which serves as a helper in the transfer process, and a second compatible binary plasmid that comprises the T-DNA border sequences flanking the heterologous nucleotide sequence of interest to be transferred to a plant host cell. In this manner, a modified T-DNA region comprising foreign DNA (the heterologous nucleotide sequence to be transferred) is constructed in a small plasmid whose origin of replication allows for stable maintenance of the plasmid in both *E. coli*. and Agrobacterium. This plasmid is transferred into *A. tumefaciens* that contains a compatible Ti plasmid (or *A. rhizogenes* that contains a compatible Ri plasmid) carrying the virulence gene. The resulting Agrobacterium-mediated binary vector transformation system has the vir functions supplied in trans to facilitate transfer of the T-DNA into the plant genome. Such binary vector Agrobacterium-mediated transformation systems and methods for their construction are well known in the art. See, for example, Hoekema et al. (1983) *Nature* 303:179–180; Simpson et al. (1986) *Plant Mol. Biol.* 6:403–415; An et al. (1988) *Plant Mol. Biol. Manual* A3:1–19; Walkerpeach and Velten (1994) *Plant Mol. Biol. Manual* B1:1–19; Komari et al. (1996) *Plant J.* 10(1):165–174; herein incorporated by reference.

The present invention provides novel compositions that are Agrobacterium strains that have been engineered to co-transfer at least two heterologous nucleotide sequences of interest, such as genes, to a recipient plant host in an independent manner. More particularly, these strains have been engineered to comprise a helper Ti (*A. tumefaciens*) or Ri (*A. rhizogenes*) plasmid that comprises the vir functions and at least two binary vector plasmids each of which comprises at least one T-DNA region. Although the helper Ti or Ri plasmid does not have to be disarmed (see, for example, An et al. (1986) *Plant Physiol.* 81:301–305), more preferably it is disarmed by deletion of the oncogenic genes to ensure that development of crown gall or hairy root disease, respectively, is prevented in the transformed plant while leaving the vir genes intact. This is accomplished by removal of the complete T-DNA region from the Ti or Ri plasmid, which may be done in the Agrobacterium strain of choice by in vivo deletion techniques (see, for example, Ooms et al. (1982) *Plasmid* 7:15–29). Because the vir genes remain intact, the disarmed helper plasmid can facilitate transfer of other T-DNA regions supplied in trans on binary vectors that have been introduced into the Agrobacterium strain.

The binary vector plasmids used in construction of the multiple-binary vector Agrobacterium strain of the present invention will each comprise at least the following standard features: 1) a broad-host-range origin of replication; 2) a multiple cloning site; 3) a selectable marker gene or genes active in both *E. coli* and Agrobacterium; 4) transfer functions (for example oriV, oriT, and trfA) that allow for transformation of Agrobacterium via conjugation (not necessary when transfer of DNA to Agrobacterium is direct, as with freeze-thaw, or via electroporation); and 5) and at least one T-DNA border region, which is preferably defined by its right and left T-DNA border sequences, although DNA transfer into the plant is enabled by the presence of only the right T-DNA border sequence; each of these T-DNA regions will also have been modified to have restriction sites for the subsequent insertion of a heterologous nucleotide sequence of interest to be transferred to the plant and subsequently integrated into the plant genome. The heterologous nucleotide sequence to be transferred and integrated will comprise at least one gene operably linked to regulatory regions that are functional within the plant, such that expression of the transferred gene can be measured to confirm successful transfer and subsequent integration of the T-DNA region derived from a particular binary vector plasmid into the plant genome. This gene may be a selectable marker gene that is functional within a plant to enable selection of transformed plants. See An et al. (1998) *Plant Mol. Biol. Manual* A3:1–19 and Walkerpeach and Velten (1994) *Plant Mol. Biol. Manual* B1:1–19 for reviews. In accordance with the present invention, at least one of the binary vector plasmids to be engineered into the Agrobacterium strain will carry a scorable marker gene within a T-DNA region, whether it be chemical selectable, visual, or assayable by some other method, such as enzyme assay, ELISA, and the like. Other sequences that facilitate the T-DNA transfer process may be incorporated within the binary vectors, including, but not limited to, an overdrive sequence (see, for example, Peralta et al. (1986) *EMBO J.* 5:1137–1142; Zyprian and Kado (1990) *Plant Mol. Biol.* 15:245–256) and a T-DNA transfer stimulator sequence (Hansen et al. (1992) *Plant Mol. Biol.* 20:113–122).

In this manner, a modified T-DNA region comprising a heterologous nucleotide sequence of interest (the sequence to be transferred to the plant cell), which has been inserted into a multiple cloning site residing between the T-DNA border sequences, is constructed in vitro within a broad-host-range plasmid. By "broad-host-range" is intended the plasmid will replicate in both *E. coli* and the Agrobacterium strain that is to be engineered. Such plasmids include, but are not limited to, plasmids belonging to the *E. coli* in groups P, Q, and W, such as pGA473 (similar to pGA472 described in An et al. (1985) *EMBO J.* 4:277–284, but with an ampicillin marker), pGA482 An et al. (1986) *Plant Physiol.* 81:86–91), pBIN 19 and its derivatives (see Frisch et al. (1995) *Plant Mol. Biol.* 27:405–409), and others as reviewed in An et al. (1988) *Plant Mol. Biol. Manual* A3:1–19. Other bacterial plasmids that can serve as the backbone of a binary vector include, but are not limited to, RSF1010-related plasmids (Bagdasarian et al. (1981) *Gene* 16 (1–3):237–247), pSa (incompatibility group W) plasmids (Leemans et al. (1983) *Gene* 19(3):361–364, and Tait et al. (1983) *Mol. Gen Genet.* 192(1–2):32–38); and endogenous Agrobacterium plasmids that are compatible with resident Ti or Ri plasmids (Jouanin et al. (1985) *Mol. Gen Genet.* 201(3):370–374).

The resulting binary vector plasmids carrying the modified T-DNA regions will be compatible with the helper Ti or Ri plasmid residing within the Agrobacterium strain that will undergo engineering. By "compatible" is intended the plasmid is able to replicate in the presence of the helper plasmid and thus coexist with the helper plasmid within the engineered Agrobacterium strain. When plasmids are able to coexist, they are stably inherited in successive generations of the bacterial strain, and thus are maintained within the bacterial strain. Plasmids are classified according to their incompatibility. Incompatible plasmids have the same origin of replication and thus compete with one another both during replication and during subsequent partitioning into daughter cells. Incompatible plasmids are able to coexist and be stably inherited in subsequent bacterial generations when selection pressure in the culture medium allows each of them to continuously replicate and be partitioned into daughter cells. Thus, for the binary vectors to be compatible with the helper Ti or Ri plasmid, their origin of replication will be different. Alternatively, their origin of replication may be the same as that of the helper plasmid, providing selection pressure in the culture medium is manipulated such that they coexist with the helper Ti or Ri plasmid resident in the Agrobacterium of choice.

Likewise, although the binary vector plasmids may all be compatible with one another, one or more of them may be incompatible with one or more of the other plasmids. Thus at least two of the binary vector plasmids may have the same origin of replication, providing selection pressure in the culture medium facilitates their coexistence. Therefore, the binary vector plasmids used in engineering the Agrobacterium strain of the present invention may have any origin of replication, including, but not limited to, RK2 oriV, pSA oriV, and pVS1ori. In one embodiment of the invention, the engineered Agrobacterium has two binary vector plasmids having the RK2 oriV origin of replication.

The binary vector plasmids will also comprise a unique bacterial selectable marker gene, which allows for selection of Agrobacterium that have successfully been engineered to contain the binary vector plasmids of interest. By "unique" is intended each binary vector plasmid will have a different bacterial selectable marker gene whose expression confers resistance to a particular selection agent, such as an antibiotic. The bacterial selectable marker gene of each plasmid resides within the backbone of the plasmid and is operatively linked to regulatory regions functional within *E. coli* and Agrobacterium. Suitable selectable marker genes are well known in the art and include, but are not limited to, genes encoding resistance to kanamycin (neomycin phosphotransferase (npt) II (Fraley et al. (1986) *CRC Critical Reviews in Plant Science* 4:1–25)), ampicillin/carbenicillin, streptomycin/spectinomycin, gentamicin, and tetracycline. The nptII gene, when operably linked to the nopaline synthase (nos) promoter and terminator, may also serve as a selectable marker in plant cells, but at much higher concentrations of selection agent (at least 500 mg/ml kanamycin sulfate in plants, versus 50 mg/ml in Agrobacterium, and 20 mg/ml in *E. coli* (see An et al. (1988) *Plant Mol. Biol. Manual* A3:1–19)). Thus, for example, culture of an Agrobacterium strain in the presence of a selection agent for gene A following transformation of that strain with a binary vector plasmid having selectable marker gene A would allow for growth of only those Agrobacteria comprising binary vector plasmids having gene A. Likewise, successful transformation of Agrobacterium with two binary vector plasmids, one of which contains selectable marker gene A and the other of which contains selectable marker gene B, would be confirmed for those Agrobacterium colonies able to grow on a medium containing both a selection agent for gene A and a selection agent for gene B. Thus presence of each binary vector in the engineered Agrobacterium is confirmed by the ability of the engineered bacteria to grow on a medium containing each of the selection agents designed to detect expression of each of the respective selectable marker genes.

Additionally, one or more of the binary vector plasmids used in the engineering the Agrobacterium strain of the invention may be a super-binary vector. See, for example, U.S. Pat. No. 5,591,616, EPA 0604662A1, and the copending application entitled "Agrobacterium-Mediated Transformation of Sorghum," U.S. patent application Ser. No. 09/056,418, filed Apr. 7, 1998, herein incorporated by reference. Such a super-binary vector has been constructed containing a DNA region originating from the virulence region of Ti plasmid pTiBo542 (Jin et al. (1987) *J. Bacteriol* 169:4417–4425) contained in a super-virulent *Agrobacterium tumefaciens*, A281, exhibiting extremely high transformation efficiency (Hood et al. (1984) *Biotechnol.* 2:702–709; Hood et al. (1986) *J. Bacteriol.* 168:1283–1290; Komari et al. (1986) *J. Bacteriol.* 166:88–94; Jin et al. (1987) *J. Bacteriol.* 169:4417–4425; Komari T. (1989) *Plant Science* 60:223–229; ATCC Accession No. 37394).

Super-binary vectors are known in the art and include pTOK162 (Japanese Patent Application (Kokai) No.

4-222527, EP-A-504,869, EP-A-604,662, and U.S. Pat. No. 5,591,616 herein incorporated by reference) and pTOK233 (Komari, T. (1990) *Plant Cell Reports* 9:303–306; and Ishida et al. (1996) *Nature Biotechnology* 14:745; herein incorporated by reference). Other super-binary vectors may be constructed by the methods set forth in the above references. Super-binary vector pTOK162 is capable of replication in both *E. coli* and in Agrobacterium. Additionally, the vector contains the virB, virC, and virG genes from the virulence region of pTiBo542. The plasmid also contains an antibiotic resistance gene, a selectable marker gene, and the nucleic acid of interest to be transferred into the plant. The nucleic acid to be inserted into the plant genome is located between the two border sequences of the T-DNA region. Super-binary vectors of the invention can be constructed having the features described above for pTOK162. Super-binary vectors are particularly useful in transformation of monocotyledonous plants (see, for example, Hiei et al. (1994) *Plant J.* 6:271–282).

Each T-DNA region of the binary or super-binary vector plasmids is constructed to have restriction sites for the insertion of the heterologous nucleotide sequence of interest to be delivered to the plant. Alternatively, the sequence to be transferred into the plant can be inserted in a T-DNA region of a binary vector plasmid by utilizing in vivo homologous recombination. See, for example, Herrera-Esterella et al. (1983) *EMBO J.* 2:987–995; Horch et al. (1984) *Science* 223:496–498). Such homologous recombination relies on the fact that the binary vector plasmid has a region homologous with a region of pBR322 or other similar plasmid. Thus, when the two plasmids are brought together a desired heterologous nucleotide sequence is inserted into the binary vector by genetic recombination via the homologous regions.

As will be evident to one of skill in the art, any nucleotide sequence of interest can be inserted into a T-DNA region of a binary vector plasmid for subsequent transformation of a plant with the multiple binary vector Agrobacterium strain of the present invention. For example, a plant can be engineered to express disease and insect resistance genes, genes conferring nutritional value, genes to confer male and/or female sterility, antifungal, antibacterial or antiviral genes, and the like. Likewise, the method can be used to transfer any nucleotide sequence to control gene expression. For example, at least one of the nucleotide sequences to be transferred could encode an antisense oligonucleotide.

Transformation technology has enabled the scientist to place inside a plant cell almost any gene of interest, and provided that the surrounding information is recognizable to that cell, that gene will be expressed in that cell. The organism's native genes may be expressed in non-normal tissues or at non-normal levels, and genes from other plants or even from other organisms, such as bacteria, Drosophila, or mammals, may also be expressed.

Various changes in phenotype are of interest including modifying the fatty acid composition in a plant, altering the amino acid content of a plant, altering a plant's pathogen defense mechanism, and the like. These results can be achieved by providing expression of heterologous products or increased expression of endogenous products in plants. Alternatively, the results can be achieved by providing for a reduction of expression of one or more endogenous products, particularly enzymes or cofactors in the plant. These changes result in a change in phenotype of the transformed plant.

Genes of interest are reflective of the commercial markets and interests of those involved in the development of the crop. Crops and markets of interest change, and as developing nations open up world markets, new crops and technologies will emerge also. In addition, as our understanding of agronomic traits and characteristics such as yield and heterosis increase, the choice of genes for transformation will change accordingly. General categories of genes of interest include, for example, those genes involved in information, such as zinc fingers, those involved in communication, such as kinases, and those involved in housekeeping, such as heat shock proteins. More specific categories of transgenes, for example, include genes encoding important traits for agronomics, insect resistance, disease resistance, herbicide resistance, sterility, grain characteristics, and commercial products. Genes of interest include, generally, those involved in oil, starch, carbohydrate, or nutrient metabolism as well as those affecting kernel size, sucrose loading, and the like.

Agronomically important traits such as oil, starch, and protein content can be genetically altered in addition to using traditional breeding methods. Modifications include increasing content of oleic acid, saturated and unsaturated oils, increasing levels of lysine and sulfur, providing essential amino acids, and also modification of starch. Hordothionin protein modifications are described in U.S. application Ser. No. 08/838,763, filed Apr. 10, 1997, now U.S. Pat. No. 5,990,389; and U.S. Pat. Nos. 5,703,049, 5,885,801, and 5,885,802, herein incorporated by reference. Another example is lysine and/or sulfur rich seed protein encoded by the soybean 2S albumin described in U.S. Pat. No. 5,850,016, and the chymotrypsin inhibitor from barley, described in Williamson et al. (1987) *Eur. J. Biochem.* 165:99–106, the disclosures of which are herein incorporated by reference.

Derivatives of the coding sequences can be made by site-directed mutagenesis to increase the level of preselected amino acids in the encoded polypeptide. For example, the gene encoding the barley high lysine polypeptide (BHL) is derived from barley chymotrypsin inhibitor, U.S. application Ser. No. 08/740,682, filed Nov. 1, 1996, and WO 98/20133, the disclosures of which are herein incorporated by reference. Other proteins include methionine-rich plant proteins such as from sunflower seed (Lilley et al. (1989) *Proceedings of the World Congress on Vegetable Protein Utilization in Human Foods and Animal Feedstuffs*, ed. Applewhite (American Oil Chemists Society, Champaign, Ill.), pp. 497–502; herein incorporated by reference); corn (Pedersen et al. (1986) *J. Biol. Chem.* 261:6279; Kirihara et al. (1988) *Gene* 71:359; both of which are herein incorporated by reference); and rice (Musumura et al. (1989) *Plant Mol. Biol.* 12:123, herein incorporated by reference). Other agronomically important genes encode latex, Floury 2, growth factors, seed storage factors, and transcription factors.

Insect resistance genes may encode resistance to pests that have great yield drag such as rootworm, cutworm, European Corn Borer, and the like. Such genes include, for example, *Bacillus thuringiensis* toxic protein genes (U.S. Pat. Nos. 5,366,892; 5,747,450; 5,737,514; 5,723,756; 5,593,881; and Geiser et al. (1986) *Gene* 48:109); lectins (Van Damme et al. (1994) *Plant Mol. Biol.* 24:825); and the like.

Genes encoding disease resistance traits include detoxification genes, such as against fumonosin (U.S. Pat. No. 5,792,931); avirulence (avr) and disease resistance (R) genes (Jones et al. (1994) *Science* 266:789; Martin et al. (1993) *Science* 262:1432; and Mindrinos et al. (1994) *Cell* 78:1089); and the like.

Herbicide resistance traits may include genes coding for resistance to herbicides that act to inhibit the action of acetolactate synthase (ALS), in particular the sulfonylurea-type herbicides (e.g., the acetolactate synthase (ALS) gene containing mutations leading to such resistance, in particular the S4 and/or Hra mutations), genes coding for resistance to herbicides that act to inhibit action of glutamine synthase, such as phosphinothricin or basta (e.g., the bar gene), or other such genes known in the art. The bar gene encodes resistance to the herbicide basta, the nptII gene encodes resistance to the antibiotics kanamycin and geneticin, and the ALS-gene mutants encode resistance to the herbicide chlorsulfuron.

Sterility genes can also be encoded in an expression cassette and provide an alternative to physical detasseling. Examples of genes used in such ways include male tissue-preferred genes and genes with male sterility phenotypes such as QM, described in U.S. Pat. No. 5,583,210. Other genes include kinases and those encoding compounds toxic to either male or female gametophytic development.

The quality of grain is reflected in traits such as levels and types of oils, saturated and unsaturated, quality and quantity of essential amino acids, and levels of cellulose. In corn, modifications of hordothionin protein for desired purposes are described in copending U.S. application Ser. No. 08/838,763, filed Apr. 10, 1997, now U.S. Pat. No. 5,990,389 and U.S. Pat. Nos. 5,703,049, 5,885,801, and 5,885,802.

Commercial traits can also be encoded on a gene or genes that could increase for example, starch for ethanol production, or provide expression of proteins. Another important commercial use of transformed plants is the production of polymers and bioplastics such as described in U.S. Pat. No. 5,602,321. Genes such as β-Ketothiolase, PHBase (polyhydroxyburyrate synthase), and acetoacetyl-CoA reductase (see Schubert et al. (1988) *J. Bacteriol.* 170:5837–5847) facilitate expression of polyhyroxyal-kanoates (PHAs).

Exogenous products include plant enzymes and products as well as those from other sources including procaryotes and other eukaryotes. Such products include enzymes, cofactors, hormones, and the like. The level of proteins, particularly modified proteins having improved amino acid distribution to improve the nutrient value of the plant, can be increased. This is achieved by the expression of such proteins having enhanced amino acid content.

For convenience, the heterologous nucleotide sequences to be transferred to the plant can be contained within expression cassettes. Such expression cassettes will comprise a transcriptional initiation region linked to the heterologous nucleotide sequence of interest. Each expression cassette is provided with a plurality of restriction sites for insertion of the nucleotide sequence to be under the transcriptional regulation of the regulatory regions.

The transcriptional initiation region, the promoter, may be native (i.e., analogous) or foreign (i.e., heterologous) to the plant host. Additionally, the promoter may be the natural sequence or alternatively a synthetic sequence. By "foreign" is intended that the transcriptional initiation region is not found in the native plant into which the transcriptional initiation region is introduced. As used herein, a chimeric gene comprises a coding sequence operably linked to a transcription initiation region that is heterologous to the coding sequence.

A variety of promoters can be used in the expression cassette. The promoters can be selected based on the desired outcome, such as to drive constitutive, inducible, or tissue-specific expression of heterologous nucleotide sequences in plants. Constitutive promoters include, for example, the core promoter of the Rsyn7 (copending U.S. application Ser. No. 08/661,601, abandoned); the core CaMV 35S promoter (Odell et al. (1985) *Nature* 313:810–812); rice actin (McElroy et al. (1990) *Plant Cell* 2:163–171); ubiquitin (Christensen et al. (1989) *Plant Mol. Biol.* 12:619–632 and Christensen et al. (1992) *Plant Mol. Biol.* 18:675–689); pEMU (Last et al. (1991) *Theor. Appl. Genet.* 81:581–588); MAS (Velten et al. (1984) *EMBO J.* 3:2723–2730); ALS promoter (U.S. application Ser. No. 08/409,297, now U.S. Pat. No. 5,659,026), and the like. Other constitutive promoters include, for example, U.S. Pat. Nos. 5,608,149; 5,608,144; 5,604,121; 5,569,597; 5,466,785; 5,399,680; 5,268,463; and 5,608,142.

Inducible promoters include, for example, those from pathogenesis-related proteins (PR proteins), which are induced following infection by a pathogen; e.g., PR proteins, SAR proteins, beta-1,3-glucanase, chitinase, etc. See, for example, Redolfi et al. (1983) *Neth. J. Plant Pathol.* 89:245–254; Uknes et al. (1992) *Plant Cell* 4:645–656; and Van Loon (1985) *Plant Mol. Virol.* 4:111–116. See also the copending application entitled "Inducible Maize Promoters", U.S. application Ser. No. 09/257,583, filed Feb. 25, 1999, herein incorporated by reference.

Of interest are promoters that are expressed locally at or near the site of pathogen infection. See, for example, Marineau et al. (1987) *Plant Mol. Biol.* 9:335–342; Matton et al. (1989) *Molecular Plant-Microbe Interactions* 2:325–331; Somsisch et al. (1986) *Proc. Natl. Acad. Sci. USA* 83:2427–2430; Somsisch et al. (1988) *Mol. Gen. Genet.* 2:93–98; and Yang (1996) *Proc. Natl. Acad. Sci. USA* 93:14972–14977. See also, Chen et al. (1996) *Plant J.* 10:955–966; Zhang et al. (1994) *Proc. Natl. Acad. Sci. USA* 91:2507–2511; Warner et al. (1993) *Plant J.* 3:191–201; Siebertz et al. (1989) *Plant Cell* 1:961–968; U.S. Pat. No. 5,750,386 (nematode-inducible); and the references cited therein. Of particular interest is the inducible promoter for the maize PRms gene, whose expression is induced by the pathogen *Fusarium moniliforme* (see, for example, Cordero et al. (1992) *Physiol. Mol. Plant Path.* 41:189–200). Other inducible promoters include the wound-inducible promoters, i.e., potato proteinase inhibitor (pin II) gene (Ryan (1990) *Ann. Rev. Phytopath.* 28:425–449; Duan et al. (1996) *Nature Biotechnology* 14:494–498); wun1 and wun2, U.S. Pat. No. 5,428,148; win1 and win2 (Stanford et al. (1989) *Mol. Gen. Genet.* 215:200–208); systemin (McGurl et al. (1992) *Science* 225:1570–1573); WIP1 (Rohmeier et al. (1993) *Plant Mol. Biol.* 22:783–792; Eckelkamp et al. (1993) *FEBS Letters* 323:73–76); MPI gene (Corderok et al. (1994) *Plant J.* 6(2):141–150); and the like, herein incorporated by reference.

Tissue-specific promoters are disclosed, for example, in Yamamoto et al. (1997) *Plant J.* 12(2):255–265; Kawamata et al. (1997) *Plant Cell Physiol.* 38(7):792–803; Hansen et al. (1997) *Mol Gen Genet.* 254(3):337–343; Russell et al. (1997) *Transgenic Res.* 6(2):157–168; Rinehart et al. (1996) *Plant Physiol.* 112(3):1331–1341; Van Camp et al. (1996) *Plant Physiol.* 112(2):525–535; Canevascini et al. (1996) *Plant Physiol.* 112(2):513–524; Yamamoto et al. (1994) *Plant Cell Physiol.* 35(5):773–778; Lam (1994) *Results Probl. Cell Differ.* 20:181–196; Orozco et al. (1993) *Plant Mol. Biol.* 23(6):1129–1138; Matsuoka et al. (1993) *Proc. Natl. Acad. Sci. USA* 90(20):9586–9590; and Guevara-Garcia et al. (1993) *Plant J.* 4(3):495–505. See also, Bevan et al. (1993) in *Gene Conservation and Exploitation: Proceedings of the 20th Stadler Genetics Symposium*, ed. Gustafson et al. (Plenum Press, New York) pp. 109–129; Brears et al. (1991) *Plant J.* 1:235–244; Lorenz et al. (1993)

Plant J. 4:545–554; U.S. Pat. Nos. 5,459,252; 5,608,149; 5,599,670; 5,466,785; 5,451,514; and 5,391,725.

The transcriptional cassette will include in the 5'-to-3' direction of transcription, a transcriptional and translational initiation region, a DNA sequence of interest, and a transcriptional and translational termination region functional in plants. The termination region may be native with the transcriptional initiation region, may be native with the DNA sequence of interest, or may be derived from another source. Convenient termination regions are available from the Ti-plasmid of *A. tumefaciens*, such as the octopine synthase and nopaline synthase termination regions. See also, Guerineau et al. (1991) *Mol. Gen. Genet.* 262:141–144; Proudfoot (1991) *Cell* 64:671–674; Sanfacon et al. (1991) *Genes Dev.* 5:141–149; Mogen et al. (1990) *Plant Cell* 2:1261–1272; Munroe et al. (1990) *Gene* 91:151–158; Ballas et al. 1989) *Nucleic Acids Res.* 17:7891–7903; Joshi et al. (1987) *Nucleic Acids Res.* 15:9627–9639.

The heterologous nucleotide sequences of interest are provided in expression cassettes inserted within the T-DNA regions of binary vectors to enable expression in the plant of interest following transformation of said plant with the engineered multiple-binary vector Agrobacterium strains of the invention. The cassette will include 5' and 3' regulatory sequences operably linked to the nucleotide sequence of interest. A given expression cassette in a T-DNA region of a given binary vector plasmid may additionally contain at least one additional gene to be co-transformed into the organism. Alternatively, the additional gene(s) can be provided on another expression cassette.

Where appropriate, the nucleotide sequence or sequences of interest may be optimized for increased expression in the transformed plant. That is, these nucleotide sequences can be synthesized using plant-preferred codons for improved expression. Methods are available in the art for synthesizing plant-preferred nucleotide sequences. See, for example, U.S. Pat. Nos. 5,380,831 and 5,436,391, and Murray et al. (1989) *Nucleic Acids Res.* 17:477–498, herein incorporated by reference.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

The expression cassettes may additionally contain 5' leader sequences in the expression cassette construct. Such leader sequences can act to enhance translation. Translation leaders are known in the art and include: picornavirus leaders, for example, EMCV leader (Encephalomyocarditis 5' noncoding region) (Elroy-Stein et al. (1989) *PNAS USA* 86:6126–6130); potyvirus leaders, for example, TEV leader (Tobacco Etch Virus) (Allison et al. (1986); MDMV leader (Maize Dwarf Mosaic Virus); Virology 154:9–20), and human immunoglobulin heavy-chain binding protein (BiP), (Macejak et al. (1991) *Nature* 353:90–94); untranslated leader from the coat protein mRNA of alfalfa mosaic virus (AMV RNA 4) (Jobling et al. (1987) *Nature* 325:622–625); tobacco mosaic virus leader (TMV) (Gallie et al. (1989) in *Molecular Biology of RNA*, ed. Cech (Liss, N.Y.), pp. 237–256); and maize chlorotic mottle virus leader (MCMV) (Lommel et al. (1991) *Virology* 81:382–385). See also, Della-Cioppa et al. (1987) *Plant Physiol.* 84:965–968. Other methods known to enhance translation can also be utilized, for example, introns, and the like.

Generally, at least one of the binary vector plasmids will comprise a T-DNA region whose heterologous nucleotide sequence comprises at least one expression cassette comprising a unique scorable marker gene that is functional within the plant. By "scorable marker gene" is intended a gene that is utilized for the selection of plant cells or tissues that have been transformed with the T-DNA insert comprising the scorable marker, which was transferred into the plant by the particular binary vector plasmid carrying the scorable marker. Plant scorable marker genes include, for example, selectable marker genes and assayable reporter genes.

Plant selectable marker genes confer resistance to a particular selection agent, and thus allow for selection of transformed cells/tissues in the presence of such a selection agent. Selectable marker genes include, but are not limited to, genes encoding antibiotic resistance, such as those encoding neomycin phosphotransferase II (NEO) (Fraley et al. (1986) CRC Critical Review in *Plant Science* 4:1–25) and hygromycin phosphotransferase (HPT or HYG) (Vanden Elzen et al. (1985) *Plant Mol. Biol.* 5:299; Shimizu et al. (1986) *Mol. Cell Biol.* 6:1074, as well as genes conferring resistance to herbicidal compounds, such as glufosinate ammonium, bromoxynil, and 2,4-dichlorophenoxyacetate (2,4-D).

By assayable "reporter gene" is intended any scorable marker gene, other than a selectable marker gene, that can be assayed for its presence and/or expression. Reporter genes generally encode a protein whose activity can be assayed to determine whether the reporter gene is present and/or is being expressed. Preferably the protein can be assayed using nonlethal methods. Use of such assayable reporter genes as opposed to selectable marker genes is disclosed in detail in the copending application entitled "Recovery of Transformed Plants Without Selectable Markers by Nodal Culture and Enrichment of Transgenic Sectors," U.S. patent application Ser. No. 08/857,664, filed May 16, 1997, now abandoned, herein incorporated by reference.

With assayable reporter genes, generally to there is some sort of chemical, biological, or physical assay available that will determine the presence or absence or change in amount of the expression product of the gene. In certain embodiments in which the assayable reporter gene produces an enzyme involved in a metabolic pathway, the assay may determine the presence or absence of, or a change in the amount of, a metabolite produced directly by the enzyme, or the presence or absence of, or a change in the amount of, a metabolite produced directly by the enzyme, or the presence or absence of, or a change in the amount of, the final product of the metabolic pathway, rather than the presence or absence of the expression product (the enzyme) itself. For example, such an enzyme might be involved in a metabolic pathway that produces oils having a particular fatty acid makeup. It will also be apparent to those of skill in the art that many forms of assay techniques are available to detect the presence and/or expression of reporter genes. For example, any expressed protein capable of detection by ELISA could be assayed by using the associated ELISA, or a modification in the amount of a specific fatty acid could be determined using the appropriate biochemical analytical technology (GCMS, for example); or a bioassay could be used (for example, expression of a crystal protein toxin from *Bacillus thuringiensis* (Bt) could be determined by screening for deleterious effects of transformed plant tissue on insects or insect larvae that are susceptible to the crystal protein toxin).

Those of skill in the art will also recognize that the presence of the assayable reporter gene can be detected directly using DNA amplification techniques known in the art, including, but not limited to PCR, RT-PCR, or LCR, for example. By way of illustration, the assayable reporter gene could be an embryo-specific gene such as a desaturase under the control of an embryo-specific promoter. Genetic modification using such a gene construct would be expected to modify seed oil profiles, without affecting expression in leaves. A properly performed PCR screen would detect the presence of the sequence in transformed plants. Those of skill in the art will recognize that when Agrobacterium-mediated transformation has been used as the transformation method, certain measures will be necessary to distinguish the assayable reporter gene present in Agrobacterium from the reporter gene present in the genome of transformed plant cells. The use of an appropriate set of primers that includes primers for Agrobacterium DNA will address this issue. It will also be recognized that any gene that can be amplified using amplification technology such as PCR can serve as an assayable reporter gene in the present invention.

Reporter genes are particularly useful to quantify or visualize the spatial pattern of expression of a gene in specific tissues. Commonly used reporter genes include, but are not limited to, B-glucuronidase (GUS) (Jefferson (1987) *Plant Mol. Biol. Rep.* 5:387); B-galactosidase (Teeri et al. (1989) *EMBO J.* 8:343–350); luciferase (Ow et al. (1986) *Science* 234:856–859); chloramphenicol acetyltransferase (CAT) (Lindsey and Jones (1987) *Plant Mol. Biol.* 10:43–52); green fluorescence protein (GFP) (Chalfie et al. (1994) *Science* 263:802); and the maize genes encoding for anthocyanin production (Ludwig et al. (1990) *Science* 247:449).

Other examples of assayable reporter genes include, but are not limited to, the oxalate oxidase gene, which has been isolated from wheat (Dratewka-Kos et al. (1989) *J. Biol. Chem.* 264:4896–4900 (the "germin" gene) and barley (WO 92/14824); the oxalate decarboxylase gene, which has been isolated from Aspergillus and Collybia (see WO 94/12622); other enzymes that utilize oxalate; other enzymes such as polyphenol oxidase, glucose oxidase, monoamine oxidase, choline oxidase, galactose oxidase, 1-aspartate oxidase, and xanthine oxidase, and the like.

As those of skill in the art will recognize, the assay for reporter genes will vary with the nature of the expression product. For example, an enzymatic assay can be used in those instances where the expression product is an enzyme, such as in the case of transformation with a gene encoding oxalate oxidase or oxalate decarboxylase. A visual or colorimetric assay would be appropriate for plant cells or tissues transformed with a GFP gene. As those skilled in the art will also recognize, when an enzymatic assay is appropriate, the existence of an assay in the art would be particularly useful. Furthermore, as noted above, other assay techniques (e.g., PCR for the assayable reporter itself, or ELISA, or a bioassay, or chemical analytical methods such as GCMS) will be appropriate in the performance of the various embodiments of the invention.

In a further alternative embodiment of the present invention, the assay can involve a procedure that measures a loss of, or a decrease in the level of expression of, a measurable product that is normally present or that is normally expressed at higher levels. For example, antisense or co-suppression technology can be used to downregulate the expression of a particular gene, and an appropriate assay that would detect the disappearance of or decease in amount of the expression product or a metabolic product can be used.

For further information on the use of scorable marker genes, see generally, Yarranton (1992) *Curr. Opin. Biotech.* 3:506–511; Christopherson et al. (1992) *Proc. Natl. Acad. Sci. USA* 89:6314–6318; Yao et al. (1992) *Cell* 71:63–72; Reznikoff (1992) *Mol. Microbiol.* 6:2419–2422; Barkley et al. (1980) *The Operon*, pp. 177–220; Hu et al. (1987) *Cell* 48:555–566; Brown et al. (1987) *Cell* 49:603–612; Figge et al. (1988) *Cell* 52:713–722; Deuschle et al. (1989) *Proc. Natl. Acad. Sci. USA* 86:5400–5404; Fuerst et al. (1989) *Proc. Natl. Acad. Sci. USA* 86:2549–2553; Deuschle et al. (1990) *Science* 248:480–483; M. Gossen (1993) Ph.D. Thesis, University of Heidelberg; Reines et al. (1993) *Proc. Natl. Acad. Sci. USA* 90:1917–1921; Labow et al. (1990) *Mol. Cell Biol.* 10:3343–3356; Zambretti et al. (1992) *Proc. Natl. Acad. Sci. USA* 89:3952–3956; Baim et al. (1991) *Proc. Natl. Acad. Sci. USA* 88:5072–5076; Wyborski et al. (1991) *Nucleic Acids Res,* 19:4647–4653; Hillenand-Wissman (1989) *Topics Mol. Struc. Biol.* 10:143–162; Degenkolb et al. (1991) *Antimicrob. Agents Chemother.* 35:1591–1595; Kleinschnidt et al. (1988) *Biochemistry* 27:1094–1104; Gatz et al. (1992) *Plant J.* 2:397–404; A. L. Bonin (1993) Ph.D. Thesis, University of Heidelberg; Gossen et al. (1992) *Proc. Natl. Acad. Sci. USA* 89:5547–5551; Oliva et al. (1992) *Antimicrob. Agents Chemother.* 36:913–919; Hlavka et al. (1985) *Handbook Exp. Pharmacol.* 78; Gill et al. (1988) *Nature* 334:721–724. Such disclosures are herein incorporated by reference.

In preparing the expression cassettes, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, for example, transitions and transversions, may be involved.

Thus, the binary vector plasmids that will be introduced into an Agrobacterium strain to construct the novel multiple-binary vector Agrobacterium strain of the present invention are modified to comprise the foregoing key features, including a broad-host-range origin of replication, a multiple cloning site, a bacterial selectable marker gene, transfer functions where necessary, and at least one T-DNA border region comprising the heterologous nucleotide sequence of interest to be transferred to a plant and subsequently integrated into the plant's genome.

At least two of these modified binary vector plasmids are introduced or transferred into an Agrobacterium strain to construct the engineered multiple-binary vector Agrobacterium strain of the present invention. A variety of Agrobacterium species and their respective strains are known in the art (particularly for dicotyledon transformation). See, for example, Hooykaas (1989) *Plant Mol. Biol.* 13:327; Hooykaas (1988) *Plant Mol. Biol. Manual* A4:1–13; Smith et al. (1995) *Crop Science* 35:301; Chilton (1993) *Proc. Natl. Acad. Sci. USA* 90:3119; Mollony et al. (1993) *Monograph Theor. Appl. Genet. NY, Springer-Verlag* 19:148; Ishida et al. (1996) *Nature Biotechnol.* 14:745; and Komari, et al. (1996) *The Plant Journal* 10:165; herein incorporated by reference. Preferably, the engineered Agrobacterium is a strain of *A. tumefaciens*, more preferably the *A. tumefaciens* strain EHA101 or EHA105, although any Agrobacterium strain may be engineered.

Methods for plasmid transfer into Agrobacterium are well known in the art. For example, the binary vector plasmids may be transferred conjugatively in a tri-parental mating into an Agrobacterium that contains a helper Ti or Ri plasmid (see, for example, Hooykaas and Schilperoort (1984) *Adv. Genet.* 22:209–283). Alternatively, sequential transformation with at least two binary vector plasmids may be achieved using the freeze-thaw method (Holsters (1978) *Mol. Gen. Genet.* 1:181–187) or electroporation method (Lalonde et al. (1989) *Am. J. Vet. Res.* 50(11) 1957–1960; Wen-jun and Forde (1989) *Nucleic Acids Res.* 17(20):8385).

Following transformation with each binary vector plasmid, bacterial colonies containing a particular binary vector plasmid or plasmids can be selected for by including a particular selection agent(s) in the growth medium that is (are) specific for the bacterial selectable marker gene(s) contained on the binary vector plasmid(s). Thus, for example, an Agrobacterium might be transformed with two binary vector plasmids, one carrying the selectable marker gene for kanamycin resistance ($kan^r$), and the other carrying the marker gene for carbenicillin resistance ($amp^r$). In this example, the Agrobacterium strain transformed with the $kan^r$ binary vector plasmid is cultured in the presence of kanamycin to select for bacterial colonies containing the selectable marker gene that confers resistance to this drug. Following this selection process, Agrobacterium colonies containing the $kan^r$ binary vector plasmid are transformed with the $amp^r$ binary vector plasmid. Following culture in a medium containing carbenicillin, carbenicillin ($amp^r$) resistant colonies are cultured in medium containing both selection agents to isolate bacterial colonies comprising both $kan^r$ and $amp^r$ binary vector plasmids. Although similar concentrations of a particular selection agent may be used in sequential rounds of selection for additional binary vector plasmids, it may be preferable to use a lower concentration of a selection agent during the first round of selection for the corresponding selectable marker gene to prevent death of colonies containing low copy numbers of the particular binary vector plasmid comprising the gene conferring resistance to the selection agent.

The resulting multiple-binary vector Agrobacterium strains provide a novel Agrobacterium-mediated gene transfer system that can be used for co-transformation of any plant, where co-transformation is achieved in a single transformation event. Transformed plants of the present invention are characterized by containing at least two independently transferred heterologous nucleotide sequences of interest, such as transferred genes, each of which are flanked by T-DNA borders and inserted in an unlinked manner within the genome of the plant. The transformed plants are normal in morphology and are fertile. Preferably, the transformed plants contain a single copy of each of the transferred nucleotide sequences with no notable rearrangements. Alternatively, the independently transferred nucleotide sequences of interest are present in the transformed plant in low copy numbers. By low copy number is intended that transformants comprise no more than five (5) copies of the T-DNA, preferably no more than three (3) copies of the T-DNA, more preferably fewer than three (3) copies of each T-DNA. In this manner, genetically modified plants, plant cells, plant tissue, seed, and the like can be obtained. Agrobacterium-mediated transformation protocols may vary depending on the type of plant or plant cell, i.e., monocot or dicot, targeted for transformation.

Agrobacterium transformation protocols are well known in the art. Agrobacterium-mediated transformation involves incubation of cells or tissues with the bacterium, followed by regeneration of plants from the transformed cells, which may or may not involve a callus formation stage. Inoculation of explants has proven to be the most effective means of creating transgenic plants.

Such explants include cells of meristematic origin, such as, for example, the primary meristems located at the apices of main and lateral shoots and roots, leaf basal meristems, nodal meristems that give rise to auxiliary shoots and roots, secondary meristems, and meristems giving rise to adventitious buds or roots. Other suitable explants include the seedling hypocotyl, immature and mature cotyledon, cotyledonary node cells, meristems from immature seed embryonic axes, immature and mature embryos, primary leaflets, and the like.

In one embodiment, the explant is a shoot apical meristem, more particularly, an intact seedling apical meristem that is obtained from an embryonic axis of a mature seed. Following seed inhibition, the meristem is exposed by removal of the primordial sheathing leaves or cotyledons and then inoculated with a multiple-binary vector Agrobacterium strain of the invention. Following Agrobacterium-mediated transformation, such an explant regenerates shoots during culture. The transformed meristem cells/tissue may be manipulated to enlarge transgenic sectors, either through selection and/or through effecting a proliferation from the tissue of shoots or multiple meristems per se. The shoot population obtained can then be screened and enriched for transgenic sectors, which are then exposed to conditions that allow for differentiation into transgenic plantlets. See particularly U.S. Pat. No. 5,736,369. In another embodiment, the explant is a meristem of a split embryonic axis obtained from mature seed as described in Malone-Schoneberg et al. (1994) *Plant Sci.* 103:199–207.

Agrobacterium-mediated transformed shoots generated from meristems, such as, for example, embryonic axis meristems, lateral or auxiliary meristems, or adventitious meristems, can be further cultured using a nodal explant method to form shoots, and ultimately plants, with enriched transgenic sectors. In this manner, shoots that assay positive for transformation are subsectioned into segments, each of which comprise an identifiable nodal junction with its associated nodal meristem. The resulting nodal explants are then cultured to induce nodal meristem development and formation of shoots with enriched transgenic sectors. Those shoots that are positive for transformation can then be cultured into transgenic plants, or used for subsequent nodal culture and enrichment prior to culturing transgenic plants. Nodal culture and enrichment of transgenic sectors is particularly effective for regeneration of transformed plants without selectable marker genes. See particularly the copending application entitled "Recovery of Transformed Plants Without Selectable Markers by Nodal Culture and Enrichment of Transgenic Sectors," U.S. patent application Ser. No. 08/857,664, filed May 16, 1997, now abandoned, herein incorporated by reference.

The engineered multiple-binary vector Agrobacterium strain can be used to transform the cells of any plant. Such cells include callus, which can be originated from any tissues of a plant. Preferably, the tissue utilized in initiating callus is immature tissue, such as immature embryos, immature inflorescences, and the basal portion of young leaves. Alternatively, the callus can be originated from anthers, microspores, mature embryos, and in principal from any other tissue capable of forming callus and/or secondary embryos.

The method can also be used to transform cell suspensions. Such cell suspensions can be formed from any plant tissue.

The method for transformation with the engineered multiple-binary vector Agrobacterium strain of the invention can be broken into several steps. The basic steps include an inoculation or infection step (step 1); a co-cultivation step (step 2) a transgenic callus and/or shoot recovery step incorporating a selection agent (for use with a plant selectable) marker gene or nonselective growth followed by screening (for use with an assayable reporter gene) (step 3); and recovery of rooted transgenic shoots followed by transfer to soil for establishment of transgenic plants (step 4).

In the infection step, the tissues or cells to be transformed are isolated and exposed to the engineered Agrobacterium strain, such as providing contact with a suspension of Agrobacterium. As noted above, each binary vector plasmid within the engineered Agrobacterium has been modified to comprise a heterologous nucleotide sequence of interest within a T-DNA region. At least one of these T-DNA regions comprises an expression cassette comprising a unique plant scorable marker gene, such as a selectable marker gene or assayable reporter gene as defined herein, for selecting or screening for transformed plants. General molecular techniques used in the invention are provided, for example, by Sambrook et al., (1989) *Molecular Cloning: A Laboratory Manual* (Cold Spring Harbor Laboratory Press, Plainview, N.Y.).

Agrobacterium containing the binary vector plasmids of interest are preferably maintained on Agrobacterium master plates with glycerol stocks frozen at −80° C. As used herein, the term "Agrobacterium capable of transferring at least two genes" refers to the engineered Agrobacterium containing the binary vector plasmids that comprise the genes or nucleotide sequences of interest and which are suitable for mediating the events required to co-transfer the genes or nucleotide sequences to the cells to be infected. Master plates can be used to inoculate agar plates to obtain Agrobacterium, which is then grown in liquid suspension cultures such as YPC, YEP, LB, MinA, with appropriate antibiotics, centrifuged, and then resuspended in an inoculation medium for use in the infection process. Such inoculation media are well known in the art and generally include the major inorganic salts and vitamins. See, for example, Chu (1987) *Proc. Symp. Plant Tissue Culture* (Science Press, Peking), pp. 43–50; Ishida et al. (1996) *Nature Biotechnology* 14:745–750; Skirvin (1981) in *Cloning Agricultural Plants Via In vitro Techniques*, ed. Conger (CRC Press, Knoxville, Tenn.), pp. 51–140; EPA 0672752A1; EPA 0687730A1; and U.S. Pat. No. 5,591,616. Alternatively, bacteria from the master plate can be used to inoculate broth cultures that are grown to logarithmic phase prior to transformation.

The concentration of engineered Agrobacterium used in the infection step and co-cultivation step can affect the transformation frequency. Likewise, very high concentrations of Agrobacterium may damage the cells or tissue to be transformed, such as primary meristems or immature embryos, and result in a reduced growth response of transformed cells. Thus, the concentration of Agrobacterium useful in the methods of the invention may vary depending on the Agrobacterium strain utilized, the tissue being transformed, the plant species being transformed, and the like. To optimize the transformation protocol for a particular plant species or tissue, the cells or tissue to be transformed (primary meristems or immature embryos, for example) can be incubated with various concentrations of Agrobacterium. Likewise, the level of scorable marker gene, expression and the transformation efficiency can be assessed for various Agrobacterium concentrations.

The cells/tissue to be transformed are generally added to the Agrobacterium suspension in a liquid contact phase containing a concentration of the engineered Agrobacterium to optimize transformation efficiencies. The contact phase facilitates maximum contact of the cells/tissue to be transformed with the suspension of Agrobacterium. Optimal length for the contact phase can be experimentally determined for the tissues and plant species undergoing transformation. Generally, the cells/tissues are contacted with the suspension of Agrobacterium for a period of at least about 5 minutes to about 60 minutes, preferably about 5 minutes to about 45 minutes, more preferably about 5 minutes to about 25 minutes, more preferably about 10 minutes to about 15 minutes.

Following the inoculation or infection step, the cells/tissue to be transformed are co-cultivated with the engineered Agrobacterium strain on a medium containing no antibiotics. Length of the co-cultivation period is determined experimentally for the type of explant, cells, or tissue and the particular plant species undergoing transformation. Generally, the cells/tissue are co-cultivated with the engineered Agrobacterium strain for about 1–30 days, preferably about 1–20 days, and more preferably about 1–10 days.

Following the co-cultivation step, the transformed cells/tissue may be subjected to an optional resting step. Where no resting step is used, an extended co-cultivation step may be utilized to provide a period of culture time prior to the addition of a selection agent, where a selectable marker gene is in use, or prior to assaying for activity of a reporter gene.

For the resting step, the transformed cells are transferred to a second medium containing an antibiotic capable of inhibiting the growth of Agrobacterium. This resting phase is performed in the absence of any selective pressures to permit preferential initiation and growth of callus, when necessary, from the transformed cells containing the heterologous nucleotide sequence. An antibiotic that is not one of the bacterial selection agents for which the engineered Agrobacterium has a resistance gene is added to inhibit Agrobacterium growth. Alternatively, the antibiotic in the selection medium may be one for which the engineered Agrobacterium strain has a corresponding resistance gene, but for which resistance is conferred only at concentrations below the concentration within the culture medium. Antibiotics that inhibit Agrobacterium are known in the art and include Cefotaxime, timetin, vancomycin, carbenicillin, and the like. Concentrations of the antibiotic will vary according to what is standard for each antibiotic. For example, concentrations of carbenicillin will range from about 50 mg/l to about 250 mg/l carbenicillin in solid media, preferably about 75 mg/l to about 200 mg/l, more preferably about 100–125 mg/l. Those of ordinary skill in the art of transformation will recognize that the concentration of antibiotic can be optimized for a particular transformation protocol without undue experimentation.

The resting phase cultures are preferably allowed to rest in the dark at 28° C. for about 1 to about 15 days, preferably for about 3 to about 10 days, more preferably for about 5 to about 8 days. Any of the media known in the art can be utilized for the resting step.

Following the co-cultivation step, or following the resting step where it is used, transformed cells/tissue are screened to select for those cells/tissues that have received and incorporated T-DNA regions comprising the heterologous nucleotide sequences of interest that have been independently introduced by the engineered Agrobacterium strain. Transformed cells/tissues are transferred to a medium that includes an antibiotic to inhibit growth of the Agrobacterium. When a plant selectable marker serves as a scorable marker gene, the medium will also include a selection agent that is specific for that plant selectable marker gene. Where the scorable marker gene is an assayable reporter gene, the cells/tissue grown on this Agrobacterium-inhibiting medium are then assayed for activity of the reporter gene. In this manner, the agent or assays used to screen transformants will thus select for transformed cells containing T-DNA inserts and their respective nucleotide sequences of interest, which comprise at least the corresponding scorable marker gene or genes and which were delivered by the Agrobacterium during transformation.

Generally, any of the media known in the art suitable for the culture of the plant of interest can be used in the screening step. During screening the transformed cells/tissues are cultured until callus and/or shoot formation is observed, depending on the type of material undergoing transformation. The calli and/or shoots are then cultured on an appropriate medium in a light/dark cycle until shoots and/or roots develop. Methods for plant regeneration are known in the art and preferred methods are provided by Kamo et al. (1985) *Bot. Gaz* 146(3):327–334, West et al. (1993) *The Plant Cell* 5:1361–1369, and Duncan et al. (1985) *Planta* 165:322–332.

Small plantlets are then transferred to tubes containing rooting medium and allowed to grow and develop more roots for approximately another week. The plants are then transplanted to soil mixture in pots in the greenhouse. Alternatively, in vitro-grown root stock can be used for grafting of the plantlets and recovery of transgenic shoots.

Further modifications may be utilized including providing a second infection step to increase infection by the Agrobacterium. Also, the vectors and methods of the invention can be used in combination with particle bombardment to produce transformed plants. Particle bombardment can be used to increase wounding in the tissues to be transformed by Agrobacterium (Bidney et al. (1990) *Plant Mol. Biol.* 18:301–313; EP0486233; herein incorporated by reference). Methods for particle bombardment are well known in the art. See, for example, Sanford et al., U.S. Pat. No. 4,945,050; Tomes et al., U.S. Pat. No. 5,879,918; Tomes et al., U.S. Pat. No. 5,886,244; Bidney et al., U.S. Pat. No. 5,932,782; Tomes et al. (1995) "Direct DNA Transfer into Intact Plant Cells via Microprojectile Bombardment," in *Plant Cell, Tissue, and Organ Culture: Fundamental Methods*, ed. Gamborg and Phillips (Springer-Verlag, Berlin); and McCabe et al. (1988) *Biotechnology* 6:923–926). Also see, Weissinger et al. (1988) *Annual Rev. Genet.* 22:421–477; Datta et al. (1990) *Biotechnology* 8:736–740; Klein et al. (1988) *Proc. Natl. Acad. Sci. USA* 85:4305–4309; Klein et al. (1988) *Biotechnology* 6:559–563 (maize); Klein et al. (1988) *Plant Physiol.* 91:440–444; Fromm et al. (1990) *Biotechnology* 8:833–839; and Hooydaas-Van Slogteren and Hooykaas (1984) *Nature (London)* 311:763–764; and Bytebier et al. (1987) *Proc. Natl. Acad. Sci. USA* 84:5345–5349; all of which are herein incorporated by reference.

After wounding of the cells by microprojectile bombardment, the cells are inoculated with Agrobacterium solution. The additional infection step and particle bombardment may be useful in enhancing transformation efficiency in those plants that are particularly recalcitrant to infection by Agrobacterium.

Transgenic plants having stably integrated T-DNA regions containing heterologous nucleotide sequences comprising coding sequences of interest other than, or in addition to, a plant scorable marker gene are identified using assays specific for the coding sequence of interest. For example, if one of the binary vector plasmids carried an expression cassette comprising a pathogen resistance gene within a T-DNA region, the presence of the transferred T-DNA in the regenerated plant could be determined by monitoring pathogen resistance in the regenerated plant.

The fact that each T-DNA region comprising heterologous nucleotide sequences of interest is integrated within the plant genome in an unlinked manner has implications for subsequent sexually reproduced generations of the initial transformed plants. Thus, sexually produced progeny of the initial transformants may retain only subsets of the originally transferred and integrated T-DNA regions. In this manner, progeny having only nonselectable coding sequences of interest, and thus loss of selectable marker genes, can be obtained through subsequent breeding practices. This is beneficial when the selectable marker gene that is desirable for initial selection of transformed plants is undesirable in the progeny of those transformed plants.

The following examples are offered by way of illustration and not by way of limitation.

EXPERIMENTAL

Example 1

Construction of Binary Plasmids

Figure 1:
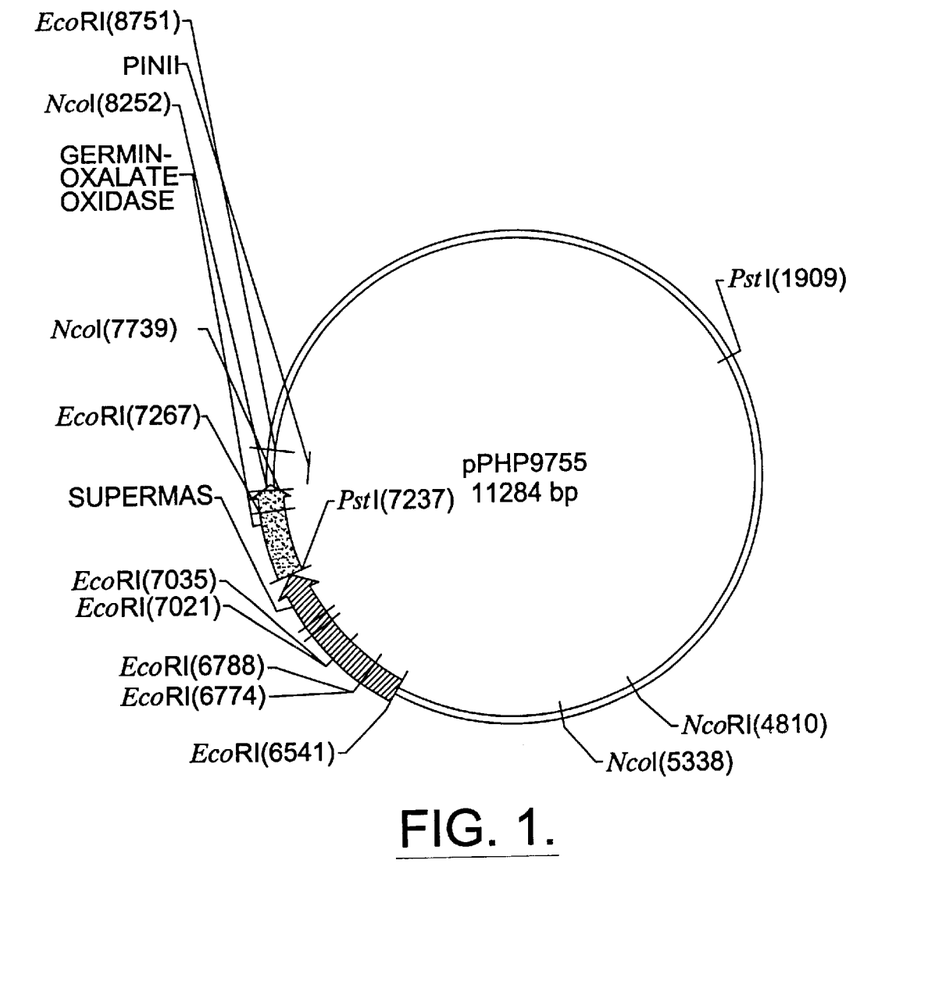
FIG. 1 provides a plasmid map of binary vector pPHP9755.
Figure 2:
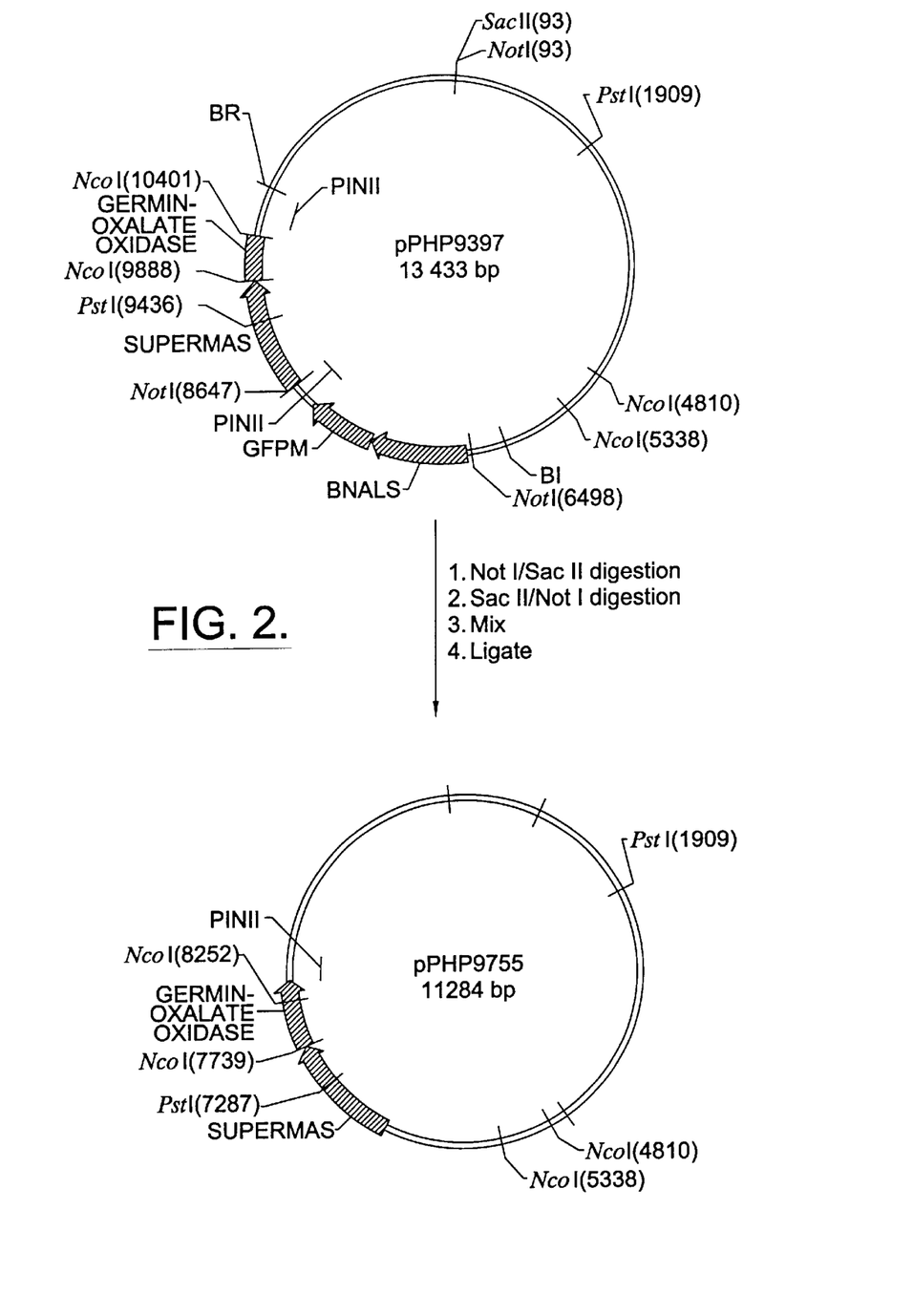
FIG. 2 provides a diagram illustrating the construction of binary vector pPHP9755.

Plasmid pPHP9755 (FIG. 1) is an Agrobacterium binary plasmid that contains the superMAS promoter ((ocs)$_3$mas from Ni et al. (1995) *Plant J.* 7:661–676) driving expression of the wheat oxalate oxidase gene (also known as germin) (Lane et al. (1991) *J. Biol. Chem.* 266:10461–10469) with the potato proteinase inhibitor II (PINII) terminator (An et al. (1989) *Plant Cell* 1:115–122). The superMAS::oxalate oxidase::pinII cassette was first assembled in a pUC plasmid backbone by ligating an NcoI site flanking the 3' end of the superMAS promoter to an NcoI overlapping the start codon of oxalate oxidase. The PINII terminator was blunt-end ligated 21 bases downstream of the stop codon of oxalate oxidase. A pBIN19 plasmid backbone (Bevan (1984) *Nucl. Acids. Res.* 12:8711–8721), with expression sequences between the T-DNA borders removed, was used for insertion of the superMAS::oxalate oxidase::PINII cassette. The cassette was oriented with the superMAS promoter proximal to the left T-DNA border. The final construction step is schematically shown in FIG. 2.

Figure 3:
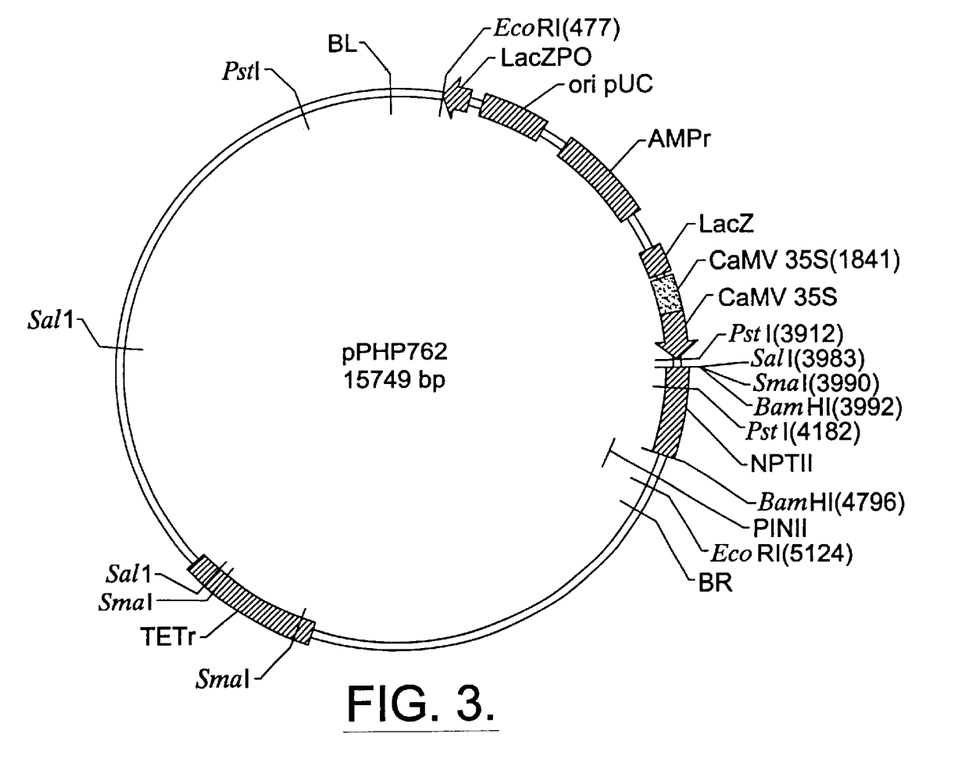
FIG. 3 provides a plasmid map of binary vector pPHP762.

Plasmid pPHP762 (FIG. 3) is an Agrobacterium binary plasmid that contains CaMV35S enhancer and promoter regions (Kay et al. (1987) *Science* 236:1299–1302) followed by the NPTII gene and potato proteinase inhibitor II (PIN II) terminator region (An et al. (1989) *Plant Cell* 1:115–122) between the right and left T-DNA borders. The NPTII gene construct was designed for constitutive expression of NPTII in plants.

Figure 4:
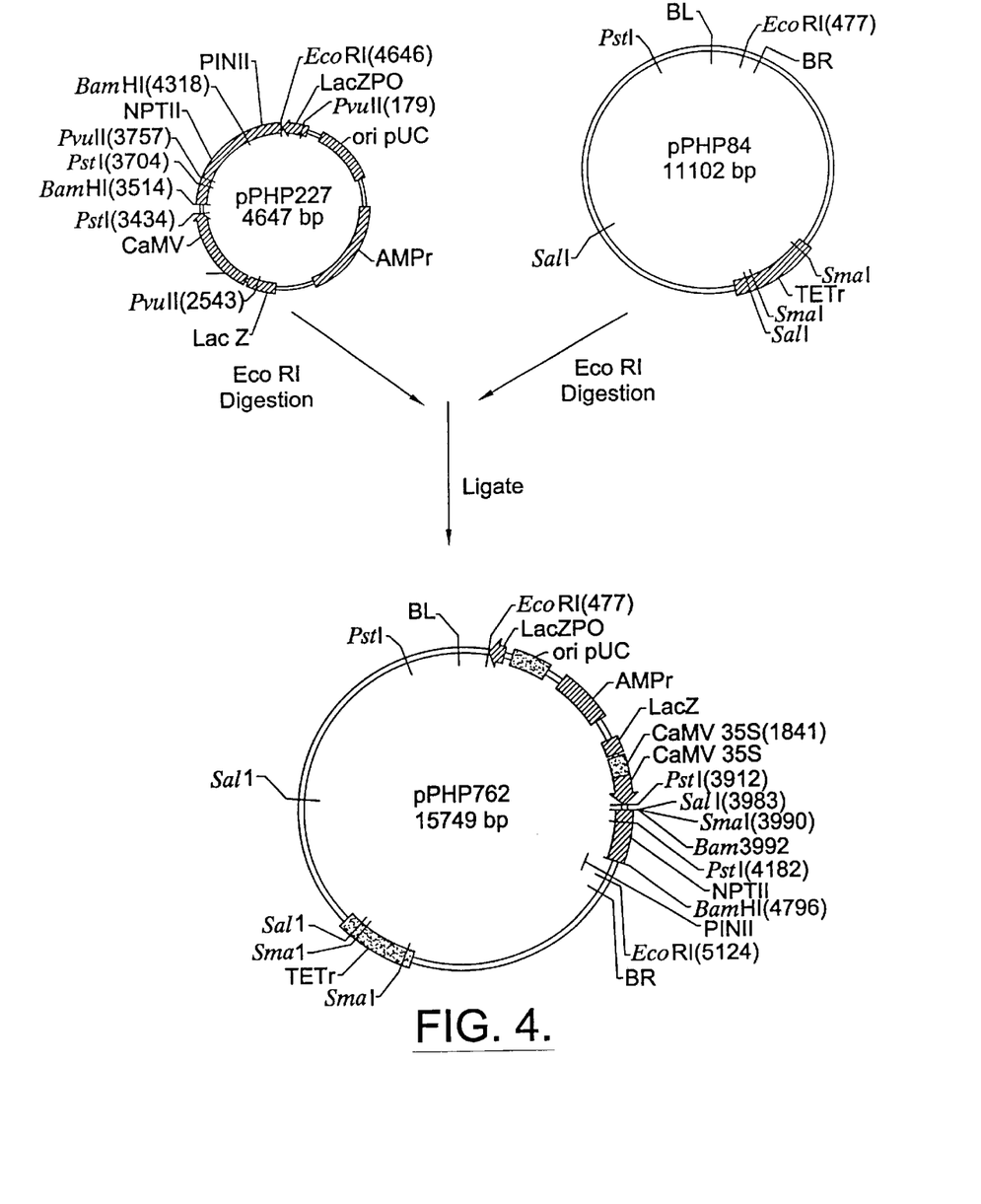
FIG. 4 provides a diagram illustrating the construction of binary vector pPHP762.

A different Agrobacterium binary plasmid was used to make pPHP762. This one was a derivative of pGA473, which is nearly identical to pGA472 published in An et al. (1985) *EMBO J.* 4:277–284, except that a CAT gene marker was placed in the T-DNA region to make pGA473. Pioneer plasmid pPHP84 was made by first removing the genes from the T-DNA region of pGA473 and then adding restriction sites to facilitate construct synthesis. Combining EcoRI-linearized pPHP227 and EcoRI partially digested pPHP84 resulted in pPHP762. This placed the full pPHP227 plasmid, containing both a plant-expressible NPTII gene and ampicillin resistance marker, between the T-DNA borders of pPHP84. The NPTII gene of pPHP227 is expressed constitutively in plants via a CaMV 35S enhancer and promoter region, and PIN II termination region. Plasmid pPHP762 was used for co-transformation experiments because it provided both the plant selectable NPTII gene and the bacterial ampicillin resistance gene to allow for differential selection of bacterial isolates containing both it and the pBIN19 vector described above. The final construction step is schematically shown in FIG. 4.

Example 2

Agrobacterium Transformation

Agrobacterium tumefaciens strain EHA105 (described in Hood et al. (1993) Transgen. Res. 2:208–218) was transformed with the kanamycin-resistant binary vector, pPHP9755 (described in Example 1) using the freeze-thaw method of Holsters et al. (1978) Mol. Gen. Genetics 1:181–187. Transformed, kanamycin-resistant, isolates were selected on solidified 60A medium with 50 mg/l kanamycin (YEP medium, 50 mg/l kanamycin). Bacterial isolates were streak purified by inoculating fresh plates of selective YEP medium. Individual colonies were picked into liquid shaking cultures of the same medium, grown to an OD600 of 1.0, and used to make glycerol-based freezer stocks, which are stored at −80° C. These stocks can be used to reinitiate Agrobacterium cultures. Liquid, shaking cultures were initiated from glycerol stocks and used for binary plasmid isolation (Qiagen Inc., Chatsworth, Calif.). Plasmid isolated from Agrobacterium was digested with restriction enzymes and compared to digested source plasmid preparations to verify that fragments were not altered in size due to the transformation procedure.

Agrobacterinum strain EHA105/pPHP9755 was sequentially transformed with the carbenicillin/ampicillin-resistant binary vector pPHP762 (described in Example 1) using the procedure above and plated on 34Z medium (LB medium, 100 mg/l carbenicillin). Carbenicillin-resistant colonies were streaked onto solid YEP plates containing 50 mg/l kanamycin and 100 mg/l ampicillin. Individual colonies were picked from these plates and inoculated into 3 ml liquid shaking cultures with kanamycin and carbenicillin. Growth in this medium was slow compared to single binary strains grown on a single antibiotic. Plasmid was isolated from putative double binary strains to verify the presence of both plasmids by gel electrophoresis of restriction-digested samples compared to original source controls. The new strain, EHA105/pPHP9755/pPHP762, was used for sunflower transformation.

Example 3

Sunflower Transformation

Sunflower transformation was achieved by a protocol involving a combination of particle bombardment followed by use of Agrobacterium inoculation for DNA delivery as described in Bidney et al. (1992) Plant Mol. Bio. 18:301–313. The double-binary vector Agrobacterium strain that was used, EHA105/pPHP9755/pPHP762, is described in Example 2. Sunflower line SMF3, described in Burrus et al. (1991) Plant Cell Rep. 10:161–166, was used in this transformation work. The explant source was dry sunflower seed, which was imbibed and dissected into split embryonic axis explants as described in Malone-Schoneberg et al. (1994) Plant Sci. 103:199–207. Procedures for preparing and treating the explants are exactly as described in Malone-Schoneberg et al. (1994) Plant Sci 103:199–207 except that a Dupont PDS-1000 helium-driven particle device was used for the particle bombardment. Explants were covered by a small piece of sterile 150 μm Nytex screen, then bombarded twice with 1.8 μm tungsten particles in this device on the highest shelf with 600 psi rupture discs and a vacuum pressure of 26 in. mercury.

The split-embryonic-axis-explant transformation procedure was done by dehulling and surface sterilizing sunflower seed, imbibing in sterile distilled water for 1–2 hr, then dissecting the seed into explants for particle bombardment and Agrobacterium treatment. Agrobacterium cultures were started the night prior to use and grown to an OD600 of 0.5 to 1.0, but usually nearer to 1.0. The bacterial suspension was centrifuged and resuspended to a final, calculated OD600 of 0.6 in inoculation medium. Particle-bombarded explants were submerged for 0.5 hr in the resuspended bacteria, then plated for a 3-d co-cultivation period on medium containing no antibiotics (Malone-Schoneberg et al. (1994) Plant Sci. 103:199–207. These plates were cultured at 26° C. for 3 d in the light. Treated explants were then transferred to medium containing antibiotics to select against Agrobacterium and positively for transformed plant tissue.

Example 4

Recovery of Segregants

In order to increase the possibility of detecting segregation of the oxalate oxidase and NPTII genes, cross pollination was done by using the T0 plant as a pollen source for male-sterile (CMS) sunflower lines and by using nontransformed SMF3 as a pollen source for the T0 plants. Pollen was harvested daily from the T0 plant for the duration of flowering. The harvest was done after the stigmas had emerged from the anther tubes but prior to stigma receptivity. Following pollen collection, the flowers were sprayed with a water-filled mister to render the remaining pollen inactive. Several hours later, the dried flowers were pollinated with nontransformed SMF3 pollen. The CMS sunflower lines were pollinated directly without the use of additional procedures.

T1 seed was harvested from mature, dried, T0 transformed plants and crossed CMS lines. The seeds were dehulled, surface sterilized (20% bleach solution containing two drops of Tween 20, 20 min) and placed in sterile petri plates containing sterile water-moistened filter discs. Seedling cotyledon and/or leaf tissue were sampled for both NPTII and oxalate oxidase enzyme analyses. Individuals showing only one activity were kept for Southern analysis and seed set.

Example 5

Enzyme Assay

Oxalate oxidase enzyme assays were set up using fresh leaf or cotyledon tissue to identify transformants. The assay method was done according to the protocol of Suigura et al. (1979) Chem. Pharm. Bull 27(9):2003–2007. The assay is a two-step reaction in which hydrogen peroxide is generated by oxalate oxidase in the first step, then detected quantitatively by a peroxidase- linked color reaction in the second. The color reaction is then measured by spectrophotometer using visible light at 550 nm.

The first step of the assay was initiated by grinding tissue in 0.1 M succinate buffer, pH 3.5. The extracts were centrifuged and supernatants were discarded. The pellet was resuspended in 0.1 M succinate buffer, pH 3.5, and 0.05 ml of an oxalic acid solution consisting of 10 mM oxalic acid dissolved in 0.1 M succinate buffer, pH 3.5. The oxalate oxidase enzyme reaction proceeded with mild agitation at room temperature (25° C.) for 4 hr. At the end of this time period, the reactions were centrifuged and an aliquot of the supernatant removed and added to a volume of 1 M Tris, pH unadjusted, to adjust the samples to a final pH of 7.0 (Tris to 0.147 M) for the second reaction step of the assay. Color development was done by adding the following components in 0.2 M Tris HCl, pH 7.0, in a mixture such that listed final concentrations were achieved: horseradish peroxidase (20 $\mu$/ml), 4-aminoantipyrine (0.165 mM), and N,N-dimethylaniline (0.33 mM). Absorbance at 500 nm was read for samples of the color development reaction. These values could be compared to a hydrogen peroxide standard curve for quantitation of the oxalate oxidase enzyme activity.

Results of these oxalate oxidase enzyme assays are shown in Table 1.

SP-0005/01 using the restriction enzymes indicated in Table 2. The digested DNA was separated by agarose gel electrophoresis and transferred to nylon membrane according to PHIAN-SP-0007/01 and PHIAN0012/01. The DNA was subsequently immobilized by UV irradiation as described in PHIAN-SP-0012/01. DNA probes specific for the oxalate oxidase gene (a.k.a. germin) or the NPTII gene coding regions were labeled with 32P by the random priming method according to PHIAN-SP-0009/01. The labeled probes were hybridized to the DNA immobilized on the nylon membrane according to PHIAN-SP-0008/01. Radioactive DNA that remained associated with the membrane after stringent washes was visualized using a Molecular Dynamics Storm Phosphor Imaging System. Images were

TABLE 1

Summary of protein analysis results from T0 and T1 transgenic sunflower plants. ELISA analysis was used for detection of NPTII protein and oxalate oxidase enzyme assay to verify the presence of that protein.

| T0/crossed plant identity | T0 Protein Results NPTII oxox* | | T1 Progeny Genetics[1] | T1 Protein Results[2] (No. Positive) | | | |
|---|---|---|---|---|---|---|---|
| | | | | oxox | oxox + NPTII | NPTII | Total |
| 610156 | positive | no data | T0 X non-transgenic | 11 | 24 | 10 | 168 |
| CS1 | Na# | na# | VK820F X 610156 | 8 | 18 | 42 | 250 |
| 610157 | positive | ? | T0 X non-transgenic | 14 | 0 | 0 | 185 |
| CS2, 12 | Na | na | VK70F X 610157 | 1 | 0 | 2 | 79 |
| 610158 | positive | positive | T0 X non-transgenic | 2 | 2 | 3 | 54 |
| 610159 | positive | positive | T0 X non-transgenic | 24 | 9 | 0 | 37 |
| CS7 | Na | na | VK820F X 610159 | 63 | 40 | 1 | 146 |
| 610160 | positive | positive | T0 X non-transgenic | 11 | 172 | 40 | 305 |
| CS6 | Na | na | VK820F X 610160 | 2 | 87 | 11 | 202 |
| 610161 | positive | negative | T0 X non-transgenic | 0 | 0 | 0 | 3 |
| 610162 | ? | negative | T0 X non-transgenic | 12 | 0 | 0 | 108 |
| CS5 | Na | na | VK70F X 610162 | 0 | 0 | 1 | 29 |
| 619165 | positive | positive | T0 X non-transgenic | 17 | 4 | 4 | 160 |
| CS3, 8, 9, 11 | Na | na | VK820F X 610165 | 37 | 35 | 22 | 545 |
| 619167 | Negative | positive | T0 X non-transgenic | 1 | 0 | 2 | 77 |
| 619168 | Positive | positive | T0 X non-transgenic | 31 | 47 | 1 | 158 |
| CS4, 10, 13 | Na | na | VK820F X 610168 | 18 | 14 | 0 | 35 |

*oxox - oxalate oxidase; #na - not applicable.
[1]T1 genetics refer to seed being obtained by crossing T0 transgenic sunflower with non-transgenic sunflower of the same variety or from crosses made with male sterile sunflower lines VK820F or VK70F using transgenics as a pollen source.
[2]Total number represents individual plants that were assayed for both oxalate oxidase enzyme activity and for NPTII protein by NPTII ELISA. Oxox are those positive only for oxalate oxidase, oxox + NPTII are those positive for both proteins, and NPTII are those individuals where only NPTII was detected.

Example 6

ELISA

NPTII ELISA assays were run on fresh leaf and cotyledon samples identical to those used for the oxalate oxidase enzyme assay. The presence of the NPTII enzyme was determined by a double-sandwich ELISA method. Tissue extracts were assayed using an immunoassay that includes antibodies specific to NPTII. Quantitative values of the enzyme in the tissue samples were determined by interpolation from a standard curve of purified NPTII protein.

Results of these assays are shown in Table 1.

Example 7

Southern Analysis

Leaf samples were lyophilized according to PHIAN-SP-0010/01. The freeze-dried material was pulverized according to PHIAN-SP-0015/01. Genomic DNA was extracted from the pulverized leaf material using a CTAB extraction buffer according to PHIAN-SP-0001/01. Purified DNA was quantitated fluorometrically as described in PHIAN-SP-0016/01. Isolated DNA was digested according to PHIANelectronically captured using Molecular Dynamics ImageQuant software. A summary of the results is shown in Table 3.

TABLE 2

Experimental design for Southern analysis.

| Restriction Enzyme | Hybridization Probe | Type | Results |
|---|---|---|---|
| Sph I | oxalate oxidase (germin) | Integration | Creates different fragments for each T-DNA integration site. |
| Spe I | oxalate oxidase (germin) | PTU | Cuts plant gene construct out of T-DNA integration site. |
| Pvu II | oxalate oxidase (germin) | Integration | Creates different fragments for each T-DNA integration site. |
| Nsi I | NPTII | Integration | Creates different fragments for each T-DNA integration site. |
| Bgl II | NPTII | Integration | Creates different fragments for each T-DNA integration site. |
| Eco RI | NPTII | PTU | Cuts plant gene construct out of T-DNA integration site. |

TABLE 3

Summary of Southern analysis results from plants recovered above that had either oxalate oxidase, NPTII, or both present.

| TO/crossed plant identity | T1 Protein Results[1] (No. Positive) T0/crossed Oxox + | | | | T1 Southern[2] Analysis oxox + | | | |
|---|---|---|---|---|---|---|---|---|
| | oxox | NPTII | NPTII | Total | oxox | NPTII | NPTII | Total |
| 610156 | 11 | 24 | 10 | 168 | 0 | 15 | 0 | 17 |
| CS1 | 8 | 18 | 42 | 250 | 0 | 8 | 0 | 8 |
| 610157 | 14 | 0 | 0 | 185 | 6 | 3 | 0 | 13 |
| CS2, 12 | 1 | 0 | 2 | 79 | 0 | 0 | 0 | 1 |
| 610158 | 2 | 2 | 3 | 54 | 0 | 2 | 0 | 5 |
| 610159 | 24 | 9 | 0 | 37 | 1 | 8 | 0 | 9 |
| CS7 | 63 | 40 | 1 | 146 | 4 | 9 | 0 | 13 |
| 610160 | 11 | 172 | 40 | 305 | 0 | 19 | 0 | 25 |
| CS6 | 2 | 87 | 11 | 202 | 0 | 6 | 0 | 13 |
| 610161 | 0 | 0 | 0 | 3 | 0 | 0 | 0 | 0 |
| 610162 | 12 | 0 | 0 | 108 | 0 | 0 | 0 | 0 |
| CS5 | 0 | 0 | 1 | 29 | 0 | 0 | 0 | 0 |
| 619165 | 17 | 4 | 4 | 160 | 0 | 0 | 0 | 0 |
| CS3, 8, 9, 11 | 37 | 35 | 22 | 545 | 0 | 2 | 0 | 3 |
| 619167 | 1 | 0 | 2 | 77 | 1 | 1 | 0 | 5 |
| 619168 | 31 | 47 | 1 | 158 | 5 | 0 | 0 | 13 |
| CS4, 10, 13 | 18 | 14 | 0 | 35 | 9 | 8 | 0 | 19 |

[1]Protein analysis is the same as that presented in Table 1 above. It is presented with the Southern analysis for direct comparisons.
[2]Total represents the total number of plants that were analyzed by Southern analysis. Each plant was hybridized with a DNA probe for the oxalate oxidase gene and for the NPTII gene. Oxox - the number of T1 progeny that had only oxalate oxidase; oxox + NPTII - number of T1 plants whose DNA hybridized to both oxalate oxidase and NPTII hybridization probes; and NPTII - those individuals that only hybridized to the NPTII probe.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed is:

1. An Agrobacterium strain comprising a helper plasmid and at least two binary vector plasmids that are stably inherited, wherein each of said binary vector plasmids comprises at least one T-DNA region comprising a heterologous nucleotide sequence of interest.

2. The Agrobacterium strain of claim 1, wherein each of said binary vector plasmids comprises a unique selectable marker gene.

3. The Agrobacterium strain of claim 1, wherein each of said binary vector plasmids has an origin of replication selected from the group consisting of RK2 oriV, pSA oriV, and pVS1ori.

4. The Agrobacterium strain of claim 2, wherein said unique selectable marker gene is a bacterial selectable marker gene.

5. The Agrobacterium strain of claim 4, wherein at least one of said binary vector plasmids comprises a plant scorable marker gene.

6. The Agrobacterium strain of claim 5, wherein said plant scorable marker gene is a plant selectable marker gene that confers resistance to a unique selection agent.

7. The Agrobacterium strain of claim 5, wherein said plant scorable marker gene is an assayable reporter gene.

8. The Agrobacterium strain of claim 3, wherein said origin of replication is RK2 oriV.

9. The Agrobacterium strain of claim 8, wherein said binary vector plasmids are P9755 and P762.

10. The Agrobacterium strain of claim 9, wherein said strain is an *Agrobacterium tumefaciens* strain.

11. The Agrobacterium strain of claim 10, wherein said strain is *Agrobacterium tumefaciens* strain EHA101 or EHA105.

12. A method for co-transformation of a plant with at least two unique heterologous nucleotide sequences of interest, said method comprising the steps of
  a) contacting a tissue from said plant with an Agrobacterium strain comprising a helper plasmid and at least two binary vector plasmids that are stably inherited, wherein each of said binary vector plasmids comprises at least one T-DNA region, wherein each of said T-DNA regions comprises one of said unique nucleotide sequences, wherein at least one of said nucleotide sequences comprises at least an expression cassette comprising a plant scorable marker gene;
  b) co-cultivating said tissue with said Agrobacterium;
  c) culturing the tissue in a culture medium comprising an antibiotic capable of inhibiting the growth of Agrobacterium;
  d) screening the tissue for expression of said plants scorable marker gene; and
  e) regenerating a transformed plant from tissue that expresses said plant scorable marker gene.

13. The method of claim 12, wherein said plant scorable marker gene is a plant selectable marker gene that confers resistance to a unique selection agent, wherein expression of said plant selectable marker gene is screened by including said unique selection agent in said culture medium.

14. The method of claim 12, when said plant scorable marker gene is an assayable reporter gene.

15. The method of claim 12, wherein said plant is a dicot.

16. The method of claim 12, wherein said plant is a monocot.

17. The method of claim 12, wherein said binary vector plasmids have an origin of replication selected from the group consisting of RK2 oriV, pSA oriV, and pVS1ori.

18. The method of claim 15, wherein said dicot is sunflower.

19. The method of claim 16, wherein said monocot is maize.

20. The method of claim 17, wherein said origin of replication is RK2 oriV.

21. The method of claim 20, wherein said binary vector plasmids are P9755 and P762.

22. The method of claim 21, wherein said strain is an *Agrobacterium tumefaciens* strain.

23. The method of claim 22, wherein said strain is *Agrobacterium tumefaciens* strain EHA101 or EHA105.

* * * * *